US010725039B2

(12) United States Patent
Richards et al.

(10) Patent No.: US 10,725,039 B2
(45) Date of Patent: Jul. 28, 2020

(54) BIOMARKER SIGNATURES FOR LYME DISEASE AND METHODS OF USE THEREOF

(71) Applicant: VERAMARX, INC., Boulder, CO (US)

(72) Inventors: Whitney Richards, Boulder, CO (US); Floyd E. Taub, Evergreen, CO (US); Robert A. Rubin, Whittier, CA (US)

(73) Assignee: VERAMARX, INC., Boulder, CO (US)

( * ) Notice: Subject to any disclaimer, the term of this patent is extended or adjusted under 35 U.S.C. 154(b) by 0 days.

(21) Appl. No.: 16/298,653

(22) Filed: Mar. 11, 2019

(65) Prior Publication Data

US 2019/0204316 A1 Jul. 4, 2019

Related U.S. Application Data

(63) Continuation of application No. 15/525,823, filed as application No. PCT/US2015/039436 on Jul. 7, 2015, now Pat. No. 10,274,491.

(60) Provisional application No. 62/021,365, filed on Jul. 7, 2014.

(51) Int. Cl.
| C12Q 1/00 | (2006.01) |
| C12Q 1/68 | (2018.01) |
| C12Q 1/56 | (2006.01) |
| C12P 21/04 | (2006.01) |
| A61K 45/00 | (2006.01) |
| G01N 33/569 | (2006.01) |

(52) U.S. Cl.
CPC ... *G01N 33/56911* (2013.01); *G01N 2333/20* (2013.01); *G01N 2800/60* (2013.01); *Y02A 50/57* (2018.01)

(58) Field of Classification Search
CPC .... A61K 38/00; A61K 38/2013; C12Q 1/689; G01N 33/86; C07K 2319/00
See application file for complete search history.

(56) References Cited

U.S. PATENT DOCUMENTS

| 9,316,652 | B2* | 4/2016 | Joosten ............ G01N 33/56911 |
| 10,274,491 | B2 | 4/2019 | Richards et al. | |
| 2011/0015154 | A1 | 1/2011 | Kellermann et al. | |
| 2011/0144914 | A1 | 6/2011 | Harrington et al. | |
| 2013/0115634 | A1 | 5/2013 | Mehra et al. | |
| 2014/0274925 | A1* | 9/2014 | Jin ............ G01N 33/56911 514/29 |
| 2015/0141279 | A1 | 5/2015 | Walzl et al. | |
| 2015/0293096 | A1 | 10/2015 | Russell et al. | |

FOREIGN PATENT DOCUMENTS

| WO | WO2011163258 A2 | 12/2011 |
| WO | WO2012039614 A1 | 3/2012 |
| WO | WO 2013110026 | 7/2013 |
| WO | WO 2016007549 | 1/2014 |
| WO | WO 2017119881 | 7/2017 |

OTHER PUBLICATIONS

Wang et al., The Jounral of Immunoglogy, 2008, 180: 8306-8315 (Year: 2008).*
BD "How to Prepare a Quality Sample" Vacutainer, Retrieved Nov. 7, 2018, 1 page, Retrieved online: www.bd.com/vacutainer/pdfs/VS8876.pdf.
BD "Tech Talk" Retrieved Nov. 7, 2018, 1 page, Retrieved online: www.bd.com/vacutainer/pdfs/techtalk/techtalk_november2005_vs7436.pdf.
CDC "Treatment " Retrieved Nov. 7, 2018, 2 pages, Retrieved online: https://www.cdc.gov/lyme/treatment/index.html.
Cerar et al. "Diagnostic value of cytokines and chemokines in lyme neuroborreliosis." Clin Vaccine Immunol. Oct. 2013;20(10):1578-84.
Extended Search report of related EP 15819031.4, dated Mar. 26, 2018, 12 pages.
Grygorczuk et al., "Concentrations of macrophage inflammatory proteins MIP-1alpha and MIP-1beta and interleukin 8 (il-8) in lyme borreliosis." Infection. Dec. 2004;32(6):350-5.
Hinckley et al., "Lyme disease testing by large commercial laboratories in the United States." Clinical Infectious Diseases. May 2014 59(5):676-81.
Hsu et al., "Differential diagnosis of annular lesions." Am Fam Physician. Jul. 15, 2001;64(2):289-96.
Mayo Clinic "Lyme Disease" Retrieved Jun. 25, 2018, 4 pages, Retrieved online: https://www.mayoclinic.org/diseases-conditions/lyme-disease/diagnosis-treatment/drc-20374655?p=1.
Ilads "Lyme Disease Quick Facts " Retrieved Nov. 7, 2018, 3 pages, Retrieved online: http://www.ilads.org/lyme/lyme-quickfacts.php.
International Search Report of parent PCT/US2015/039436, dated Oct. 6, 2015, 8 pages.
International Search Report of related PCT/US2016/012387, dated Mar. 11, 2016, 10 pages.
Nopper et al., "When it's not ringworm: annular lesions of childhood." Pediatr Ann. Mar. 1998;27(3):136-48.
Soloski et al., "Serum inflammatory mediators as markers of human Lyme disease activity." PLoS One. Apr. 16, 2014;9(4):e93243.
Aucott et al., "CCL19 as a Chemokine Risk Factor for Posttreatment Lyme Disease Syndrome: a Prospective Clinical Cohort Study." Clin Vaccine Immunol. Sep. 6, 2016;23(9):757-66.
Gautam et al., "Interleukin-10 alters effector functions of multiple genes induced by Borrelia burgdorferi in macrophages to regulate Lyme disease inflammation." Infect Immun. Dec. 2011;79(12):4876-92.
Kowarik et al., "CXCL13 is the major determinant for B cell recruitment to the CSF during neuroinflammation." euroinflammation. May 16, 2012;9:93, 11 pages.
Li et al., "Borrelia burgdorferi lacking BBK32, a fibronectin-binding protein, retains full pathogenicity." Infect Immun. Jun. 2006;74(6):3305-13.

(Continued)

*Primary Examiner* — Gary B Nickol
*Assistant Examiner* — Lakia J Jackson-Tongue
(74) *Attorney, Agent, or Firm* — Casimir Jones, S.C.; David Casimir

(57) ABSTRACT

The present invention relates to methods for the diagnosing, prognosing, monitoring, differentiating, treating, and managing of Lyme disease in a subject. The methods according to the invention are characterized by the detection of a biomarker signature comprised of a combination of two or more analytes indicative of disease.

8 Claims, No Drawings

(56) References Cited

OTHER PUBLICATIONS

Niddam et al., "Plasma fibronectin stabilizes Borrelia burgdorferi-endothelial interactions under vascular shear stress by a catch-bond mechanism." Proc Natl Acad Sci U S A. Apr. 25, 2017;114(17):E3490-E3498.
Steere et al., "The emergence of Lyme disease." J Clin Invest. Apr. 2004;113(8):1093-101.
Szczepanski et al., " Interaction between Borrelia burgdorferi and endothelium in vitro." J Clin Invest. May 1990;85(5):1637-47.
Vechtova et al., "A bite so sweet: the glycobiology interface of tick-host-pathogen interactions." Parasit Vectors. Nov. 14, 2018;11(1):594.
Search Report of related EP Application No. 16884097.3, dated Nov. 25, 2019, 16 pages.

\* cited by examiner

BIOMARKER SIGNATURES FOR LYME DISEASE AND METHODS OF USE THEREOF

CROSS REFERENCE

This application is a continuation of U.S. patent application Ser. No. 15/525,823, filed May 10, 2017, now U.S. Pat. No. 10,274,491, issued Apr. 30, 2019, which is a U.S. 371 national phase entry of International Patent Application No. PCT/US2015/039436, filed Jul. 7, 2015, which claims priority to U.S. Provisional Patent Application Ser. No. 62/021,365 filed Jul. 7, 2014, the disclosure of which is herein incorporated by reference in their entireties.

FIELD OF THE INVENTION

The present invention relates to the field of medical diagnostics and treatment, and the use of biomarkers in the determination of early Lyme disease ("LD") infection, and more specifically, a LD biomarker signature indicative of LD infection, and more specifically within the first eight weeks after infection. The present invention relates to a method for diagnosing and treating LD in a subject using the determination of expression levels of at least two, and preferably, a plurality, of biomarkers, e.g., cytokine or other host biochemical.

BACKGROUND OF THE INVENTION

Lyme disease is the most common vector born infectious disease in North America, Asia and Europe. It is a multisystem, inflammatory, progressive disease with a wide range of clinical manifestations, sometimes including erythema migrans ("EM") the initial and readily recognized cutaneous "target" lesion. From EM, which may only present in an estimated 23% of the patients, it may disseminate to other organs, including the nervous system, joints, and heart. Such progression may result in permanent neurological and/or musculo skeletal damage, and debilitating symptoms including fatigue and other flu-like symptoms.

A diagnosis of LD is currently based on clinical symptoms and serology, i.e., antibody to LD. The latter may not be detectable during the first few weeks of infection. The current LD diagnosis methodology uses a recommended two-tier serological assay, misses up to 60% of early infections, and is unable to distinguish a past infection from current, active *Borrelia* infection. More specifically, current sero-diagnostic assays include an ELISA assay to detect antibodies to *Borrelia* species followed by a Western blot for confirmation. If diagnosed in the early stages, the disease can generally be cured with therapeutic agents, e.g., antibiotics. If left untreated, complications involving joints, the heart, and the nervous system can occur. It is therefore crucial to be able to specifically detect and diagnose Lyme disease at an early stage in order to avoid complications that may develop in later stages. The instant invention includes a method that employs two or more biomarkers to diagnose and treat early LD, where early LD is defined at less than or equal to eight weeks from infection/exposure.

Due to the fact that few spirochetes are present, i.e., *Borrelia burgdorferi*, the spirochete that causes LD, especially in blood specimens, the best current methods measure immune response. While not fully reviewed here, many steps, including antigen capture by "professional antigen presenting cells" and numerous signaling and processing steps, as well as coordination of various immune cell types, are required prior to production of Ab. For example, prior to Ab secretion numerous immune signaling agents must be secreted and transported from one type of immune cell to another. An immune network including APCs, T-cells of various types and B-cells is generated. Even once these signals are generated numerous steps of B-cell maturation, transcription, translation, processing and secretion are required before even low levels of IgM Ab are present in the blood. Evolution has driven the spirochete to attempt to evade and suppress the Ab response, and numerous steps between the APC and the Ab provide many possible opportunities for suppression. Certain subjects, i.e., genotypes, may also be less effective in promptly completing the process and producing high levels of Ab. Thus, measurement of the earliest steps of immune response, prior to antibody excess that can be measured in the blood, is rationally expected to a more sensitive method of detecting early infection.

Although the Ab response may be delayed or weak, a significant number of acute Lyme disease patients have such a florid early immune response that it may be visible with the naked eye as erythema migrans (EM). It is known that some clinicians may miss EM, and some skin types may not show the response. Further, it should be noted that EM detected clinically may not be indicative of Lyme disease. For examples of descriptions and differential diagnosis based on apparent EM, see, e.g., Hsu (2001) Am Fam Physician 64(2):289; and, Nopper (1998) Pediatr Ann 27:136. Other symptoms of initial Lyme disease including, fever, malaise, arthralgia, headache and stiff neck are even less specific than EM.

The significant disadvantages (poor sensitivity and specificity) of current assays lead to a significant medical need for better diagnostic tests for diagnosing and treating early Lyme disease. There are some methods that culture blood cells and look for cytokine production in response to antigens for the detection of LD, however these are expensive, labor intensive, rely on artful methods and require living white blood cells. Molecular methods of identifying the immune mediators that can "see" the early immune response, even when the naked eye, historically an insensitive system, cannot see a skin lesion, are targeted in the present invention because molecular methods typically are more sensitive than clinical observation in detecting immune responses.

Hence, there remains a need for early identification and/or diagnosis and/or treatment of LD via molecular methods, and specifically via biomarkers that can be easily assayed using ELISA type assays common in the clinical lab. Identification of biomarkers associated with LD may also aid in identification of key molecular pathways that may be targeted for therapeutic purposes. More specifically, biomarker analysis can provide prognostic as well as diagnostic information, guide initial treatment choice, monitor treatment efficacy, and improve outcomes. The two or more biomarkers, hereinafter referred to as the biomarker signature, of the instant invention allow specifically for early disease diagnosis, effective treatment, and progression prevention. Early diagnosis, appropriate treatment, and prevention of progression and/or recurrence, and biomarker testing can play a role in all of these management areas. The poor sensitivity and specificity of the current methods for detecting acute LD means that methods for the diagnosing, prognosing, monitoring, differentiating, treating, and managing of Lyme disease in a subject characterized by the detection of a biomarker signature comprised of a combination of two or more analytes indicative of disease would be an invaluable tool to aid clinicians. Such methods have the potential to expedite and increase the accuracy of LD diagnosis and treatment.

A method such as discussed herein, that uses, for example, serum, plasma, blood, blood spots, blood filtrate, urine, saliva or tears, detects the in vivo production of the biomarker signature, i.e., cytokine or other analyte markers, would be easier, more generally applicable, and more accurate that those currently available. Both highly specific and more sensitive tests detecting biomarker signatures may also have value as a component of a multi-tier LD assay. Such a biomarker assay would be more sensitive and more specific than current serological assays, and would provide detection and diagnosis at early time points, i.e., earlier than detection of antibodies. The present invention is an effective diagnostic method for LD that improves disease outcomes in patients through early detection and supporting early treatment.

SUMMARY OF THE INVENTION

To overcome the low rates of success using the current 2-tier methodology and subsequent treatment, provided herein, are methods for diagnosing and treating LD, wherein the presence of the biomarker signature indicates existence of LD. Said method includes detection of a biomarker signature, said biomarker signature comprises a combination of two or more biomarkers selected from a discrete group of biomarkers, the group comprising IL.1B, IL.2, IL.4, IL.6, IL.8, IL.10, IFN.g, MCP.1, TNF.a, VEGF, CRP, IL.5, GM.CSF, MIP.1a, MIG, b.NGF, IP.10, MIP.1b, Ferritin, Fibrinogen, SAA, CCL19, PDGF.bb, Procalcitonin, and CTACK. Biomarker signatures create a "fingerprint" to diagnosis and treatment for a subject.

According to the present invention, provided are biomarker signatures and related methods for diagnosing and treating LD. The present invention, therefore, provides a method of diagnosing and treating a subject suspected of LD infection. The present invention provides a method of diagnosing and treating LD in a subject comprising the steps of:

obtaining a sample from the subject;

detecting in the sample the presence of a biomarker signature; and administering a therapeutic treatment to the subject based on the biomarker signature detection results.

In some embodiments, detecting the presence of the biomarker signature comprises generating a complex between at least one detection agent and two or more analytes.

In some embodiments, the biomarker signature comprises a combination of two or more analytes comprising cytokines, chemokines, prostaglandins, immune response markers, complement components, or host response factors. In some embodiments, the two or more analytes are selected from the group consisting of IL.1B, IL.2, IL.4, IL.6, IL.8, IL.10, IFN.g, MCP.1, TNF.a, VEGF, CRP, IL.5, GM.CSF, MIP.1a, MIG, b.NGF, IP.10, MIP.1b, Ferritin, Fibrinogen, SAA, CCL19, PDGF.bb, Procalcitonin, and CTACK. In some embodiments, the two or more analytes consist of CRP, IL.5, GM.CSF, and MIP.1a, or IL.1B, IL.2, IL.4, IFN.g, VEGF, and CRP, or of IL1.B, IL.6, CRP, MIG, b.NGF, IP.10, MIP.1b, Ferritin, Fibrinogen, SAA, and CCL19, or IL.1B, IL.2, IL.4, IL.6, IL.8, IL.10, IFN.g, MCP.1, TNF.a, VEGF, and CRP, or CRP, IL.5, GM.CSF, MIP.1a, CTACK, and Procalcitonin.

In some embodiments, the two or more analytes consist of IL.1B, IL.6, and CRP and at least one additional biomarker selected from the group consisting of IL.2, IL.4, IL.8, IL.10, IFN.g, MCP.1, TNF.a, VEGF, IL.5, GM.CSF, MIP.1a, MIG, b.NGF, IP.10, MIP.1b, Ferritin, Fibrinogen, SAA, CCL19, PDGF.bb, Procalcitonin, and CTACK.

In some embodiments, an output value biomarker signature score is derived using a statistical algorithm or algorithms to produce a score being indicative of the probability the subject has Lyme disease.

In some embodiments, a method of diagnosing and treating a subject suspected of Lyme disease infection, comprising the steps of: obtaining a sample from the subject; detecting in the sample the presence of a biomarker signature; translating the presence of a biomarker signature into an output value biomarker signature score, wherein the output value score is derived using a statistical algorithm or algorithms, the score being indicative of the probability of the subject having Lyme disease; determining Lyme disease status based on the biomarker signature output value score; and administering a therapeutic treatment to the subject only if the subject is determined to be infected with Lyme disease based on the resulting biomarker signature output value score.

In another embodiment, a method is for treating Lyme disease in a subject is provided, which comprises the steps of: requesting an assay of a sample obtained from a subject, said assay capable of determining a biomarker signature indicative of Lyme disease, wherein said biomarker signature comprises two or more analytes; and administering therapeutic treatment to the subject if the results indicate Lyme disease.

Another embodiment encompasses a method for determining the need for treatment of Lyme disease in a subject, comprising the steps of: performing an assay of a sample obtained from a subject to determine results indicating the presence of a biomarker signature indicative of Lyme disease, and providing the results of the assay indicating the presence or absence of the biomarker signature, and further comprise the determination of a score.

In some embodiments, a method for determining the need for treatment of Lyme disease in a subject comprising the steps of: analyzing assay results of an assay indicating whether or not a subject sample has a biomarker signature indicative of Lyme disease infection, and administering therapeutic treatment to the subject for Lyme disease based on the assay results.

In some embodiments, a method of identifying a subject suspected of Lyme disease infection as being likely to benefit from therapeutic treatment or not likely to benefit from therapeutic treatment, comprising the steps of: determining analyte concentrations comprising a biomarker signature in a sample obtained from the subject, inputting analyte concentration values into a statistical algorithm or algorithms to produce an output value score indicative of the probability the subject has Lyme disease, wherein a score indicative of the probability of having Lyme disease is indicative of the subject being likely to benefit from treatment.

Another embodiment includes a kit for performing an assay diagnosing Lyme disease comprising: a substrate comprising at least one probe for the two or more corresponding analytes selected from the group consisting of IL.1B, IL.2, IL.4, IL.6, IL.8, IL.10, IFN.g, MCP.1, TNF.a, VEGF, CRP, IL.5, GM.CSF, MIP.1a, MIG, b.NGF, IP.10, MIP.1b, Ferritin, Fibrinogen, SAA, CCL19, PDGF.bb, Procalcitonin, and CTACK; and, instructions for performing the diagnostic assay.

A biomarker signature is defined by a combination of two or more biomarkers (a.k.a., analytes) and is indicative of the relative likelihood of infection, and in turn, the likelihood of response to treatment. A biomarker may be, e.g., a cytokine, a chemokine, prostaglandin, immune response markers, complement component, or a host response protein or non-protein factor.

In some embodiments, a biomarker signature comprises combination of two or more biomarkers selected from the group consisting of IL.1B, IL.2, IL.4, IL.6, IL.8, IL.10, IFN.g, MCP.1, TNF.a, VEGF, CRP, IL.5, GM.CSF, MIP.1a, MIG, b.NGF, IP.10, MIP.1b, Ferritin, Fibrinogen, SAA, CCL19, PDGF.bb, Procalcitonin, and CTACK.

In a preferred embodiment, the two or more biomarkers selected comprise a combination of four biomarkers, wherein the four biomarkers consist of CRP, IL.5, GM.CSF, and MIP.1a.

In a more preferred embodiment, the two or more biomarkers selected comprise a combination of six biomarkers, wherein the six biomarkers consist of IL.1B, IL.2, IL.4, IFN.g, VEGF, and CRP, or CRP, IL.5, GM.CSF, MIP.1a, CTACK, and Procalcitonin.

In a more preferred embodiment, the two or more biomarkers selected comprise a combination of eleven biomarkers, wherein the eleven biomarkers consist of IL1.B, IL.6, CRP, MIG, b.NGF, IP.10, MIP.1b, Ferritin, Fibrinogen, SAA, and CCL19.

In an even more preferred embodiment, the two or more biomarkers selected comprise a combination of eleven markers, wherein the eleven markers consist of IL.1B, IL.2, IL.4, IL.6, IL.8, IL.10, IFN.g, MCP.1, TNF.a, VEGF, and CRP.

In another embodiment, the two or more biomarkers selected comprise a combination IL.1B, IL.6, and CRP and at least one additional biomarker selected from the group consisting of IL.2, IL.4, IL.8, IL.10, IFN.g, MCP.1, TNF.a, VEGF, IL.5, GM.CSF, MIP.1a, MIG, b.NGF, IP.10, MIP.1b, Ferritin, Fibrinogen, SAA, CCL19, PDGF.bb, Procalcitonin, and CTACK.

In some embodiments, the method further comprises determining a biomarker signature score that is indicative of the likelihood (probability) of the presence or absence of LD.

In some embodiments, the present invention biomarker signature score may be combined with evidence of the LD spirochete obtained by physical methods such as mass spectrometry, biochemical methods such as polymerase chain reaction, or biological methods such as antibody production in vivo.

In some embodiments, the present invention biomarker signature score is combined with the above LD evidence, and further combined with the production of biomarkers in vitro.

The present invention includes an assay, and/or a kit, and/or a set of reagents for diagnosing early LD in a subject comprising: at least one probe or pair of reagents, which may include antibodies, aptamers or other biomarker binding materials, and beads or plates or other substrates or homogeneous (non-substrate) binding reactions for the detection of one or a combination of two or more biomarkers, wherein some embodiments said biomarkers are selected from the group consisting of IL.1B, IL.2, IL.4, IL.6, IL.8, IL.10, IFN.g, MCP.1, TNF.a, VEGF, CRP, IL.5, GM.CSF, MIP.1a, MIG, b.NGF, IP.10, MIP.1b, Ferritin, Fibrinogen, SAA, CCL19, PDGF.bb, Procalcitonin, and CTACK. In certain embodiments, the kit further includes agents that generate detectable signals, such as, light, absorption of light, fluorescence, enzyme reactions, electrochemical changes, plasmon resonance, magnetic signals, interference patterns or other signals known in the art. In certain embodiments, the substrate may be a glass slide and the apparatus may comprise a microarray. Some embodiments use homogeneous assays that include fluorescent quenching or other methods know in the art. Some embodiments use precipitation or other methods know in the art to measure the binding of a molecular probe to a biomarker. In some embodiments the binding of the biomarker to such a probe on a specialized surface changes the electric, physical or optical properties of that surface allowing detection of the binding event. The binding may be increased by addition, simultaneously or subsequently, of a second reagent, which may also contain easily detectable signal generators known in the art. In some embodiments biomarkers are detected simultaneously in "multiplexed" assays.

DETAILED DESCRIPTION OF THE INVENTION

The present invention relates to biomarker signature based methods for the diagnosing, prognosing, monitoring, differentiating, treating, and managing of Lyme disease in a subject, wherein a biomarker signature is comprised of a combination of two or more analytes.

Biomarkers

A biomarker is a biological indicator from a subject, that individually, or more likely in combination with other biomarkers, reflects the absence, presence, or the condition of a disease and/or especially the host response to that disease. Biomarkers may reflect a variety of disease characteristics, including the level of exposure to an environmental or genetic trigger, an element of the disease process itself, and intermediate stage between exposure and disease onset, or an independent factor associated with the disease state, but not causative of pathogenesis. Biomarkers may be used to determine the status of a subject or the effectiveness of a treatment. Biomarker combinations with the most diagnostic utility have both high sensitivity and specificity. In practice, biomarkers and/or specific combinations of biomarkers having both high sensitivity and specificity are not obvious. Evaluation, assessment, and combination of specific biomarkers for diagnosis provide an improved approach to disease treatment.

Biomarker Examples: Cytokines, Acute Phase Reactants, and Complement Factors

Cytokines, prostaglandins, acute phase reactants, and complement factors are examples of biomarkers indicative of a subject's response to infection, immune responses, inflammation, and trauma. Cytokines include, for example, chemokines, interferons, interleukins, lymphokines, and other immune signaling molecules. Biomarker is, for purposes of this application, defined as a measurable substance in a sample from a subject, whose level is indicative of some phenomenon such as normal biologic processes, pathogenic processes, disease, infection, exposure, or response. Biomarkers include, e.g., cytokines, immune response markers, complement components, and/or other circulating host factors regulated by the immune system.

Therefore, this invention has identified biomarker signatures that enable a distinction between control and LD, the identification of subjects likely to respond to treatment. It has been determined that, contrary to the fact that a biomarker may have virtually no predictive value alone, in combination biomarkers identified as a signature carry great utility as derived, "secondary" biomarkers wherein the information is provided based on combination. Biomarker signatures that may be relevant to disease diagnosis and treatment, include a combination of two or more, preferably 4-8, and more preferably 10-12 biomarkers chosen from the group consisting of 4-1BB, A-2-macroglobulin, ACE-2, ActivinA, Adiponectin, Adiposin, AgRP, ALCAM, Alpha-fetoprotein, Amphiregulin, Angiogenin, Angiopoietin 1, Angiopoietin 2, Angiostatin, ANGPTL4, Aβ40, Aβ42, Ax1, B7-1(CD80), BCAM, BCMA, BDNF, beta IG-H3, CA19-9, Carbonic Anhydrase IX, Cardiotrophin-1, CathepsinS, CCL1/I-309, CCL14/HCC-1/HCC-3, CCL14a, CCL14/mip-1 delta/LKN-1, CCL17/TARC, CCL18/PARC, CCL19/MIP3B, CCL20/MIP-3 alpha, CCL21/6Ckine, CCL22/MDC, CCL26/Eotaxin-3, CCL28, CCL3/CCL4 (MIP-1 ALPHA/MIP-1 beta), CD14, CD23, CD30, CD40, CD40 Ligand, CEA, CEACAM-1, Chemerin, CKb8-1, CNTF, C-peptide, Cripto, CRP, CTACK, CX3CL1/Fractalkine, CXCL12/SDF-1, CXCL16, CXCL17NCC-1, CXCL4/PF4, CXCL5/ENA-78, CXCL7/NAP-2, DAN, Decorin, DKK-1, Dkk-3, Dkk-4, DPPIV, DR6(TNFRSF21), Dtk, E-Cadherin, EDA-A2, EGF, EGFR, EG-VEGF, Endoglin, Eotaxin, Eotaxin-2, EpCAM, ErbB2, ErbB3, Erythropoietin R, E-Selectin, Fas Ligand, Fas/TNFRSF6, Fc gamma RIIB/C, Ferritin, FGF basic, FGF-4, FGF-6, FGF-7, FGF-9, Fibrinogen, FLRG, Flt-3 Ligand, Follistatin, FSH, Furin, Galectin-7, GCP-2, GDF-15, GDNF, GITR, GITR-Ligand, GM-CSF, GRO, Growth Hormone, HB-EGF, HCC-4, hCG intact, HGF, HVEM, 1-309, ICAM-1, ICAM-2, ICAM-3, IFN-a2, IFN-g, IFNα, IGF-1, IGF-1sR, IGF-2, IGFBP-1, IGFBP-2, IGFBP-3, IGFBP-4, IGFBP-6, IL-10, IL-10R alpha, IL-10R beta, IL-11, IL12/IL23-p40, IL-12p40, IL-13, IL-13R alpha2, IL-13R1, IL-15, IL-17, IL-17A, IL-17B, IL-17C, IL-17F, IL-17R, IL-18, IL-18BP alpha, IL-18R beta, IL-1a, IL-1B, IL-1R4/ST2, IL-1ra, IL-1RI, IL-1RII, IL-2, IL-21, IL-21R, IL-22, IL-23, IL-25, IL-28A, IL29, IL-2Ra, IL-2Rbeta, IL-2Rgamma, IL-3, IL-31, IL-33, IL-4, IL-5, IL-5Ralpha, IL-6, IL-6R, IL-7, IL-8, IL-9, Insulin, IP-10, I-TAC, Latency Associated Peptide of TGF beta 1, Leptin, Leptin R, LIF Light, LIMPII, L-Selectin, Luteinizing hormone, LYVE-1, Marapsin, MCP-1(MCAF), MCP-2, MCP-3, MCP-4, M-CSF, M-CSFR, MICA, MICB, Midkine, MIF, MIG, MIP-1a, MIP-1b, MMP-1, MMP-10, MMP-13, MMP-2, MMP-3, MMP-7, MMP-8, MMP-9, MMP-9, MPIF-1, MSP-a, NCAM-1, NGFR, Nidogen-1, NrCAM, NRG1-beta1, NT-3, NT-4, Oncostatin M, Osteopontin, Osteoprotegerin, PAI-I, PDGF-AA, PDGF-AB, PDGF-bb, PDGFR beta, PDGFRalpha, PECAM-1, PLGF, Procalcitonin, Prolactin, PSA, PSA-free, PSA-total, RAGE, RANK, RANTES, Resistin, S-100b, sCD40L, SCFR, SCGF-b, SDF-1a, SDF-1 beta, Serum Amyloid A, sgp130, ShhN, Siglec-5, Siglec-9, Soluble IL-2 Receptor a sIL-2Ra, Soluble IL-6 Receptor sIL-6R, Soluble TNF, Receptor I sTNFRI, Soluble TNF Receptor II sTNFRII, sTNFRI, sTNFRII, TACE, Tau, TECK, TGF beta, TGF beta1, TGFalpha, TGFbeta2, TGFbeta3, Thrombopoietin, Thyroglobulin, Tie-1, Tie-2, TIM-1, TIMP-1, TIMP-2, TIMP-4, Tissue Plasminogen Activator, TNF receptors, TNF-a, TNF-b, TRAILR2, TRAILR3, TRAILR4, Trappin-2, TREM-1, Troponin-I, TSH, TSLP, Ubiquitin+1, uPAR, VCAM-1, VE-Cadherin, VEGF, VEGF-A, VEGF-C, VEGF-D, VEGFR2, VEGFR3, XCL1/Lymphotactin, and XEDAR. The group from which biomarkers may be selected may further include C4a and C3a complement split products, e.g., Complement factors including but not limited to those of the Classical pathway, C1 complex, C1q, C1r, C1s, C4, C2; the Lectin pathway, MBL, MASP-1, MASP-2; the Alternative pathway; C3, Factor B, Factor D, Properdin 20; the Membrane attack complex, C5, C6, C7, C8, C9; Control proteins, C1 inhibitor, C4 binding protein, Factor I, Factor H; Receptor/membrane proteins, Decay-accelerating factor, Homologues restriction factor; and Anaphylatoxin receptors, C3a/C4a, C5a, C3 binding proteins, CR1, CR2, CR3, and CR4. The group from which biomarkers may be selected may further include Arachidonic acid, leukotrienes (A4, C4, D4 AND E4), prostoglandins (PGD2, PGE2, PDF2, PGH2, PGI2, PGF1Alpha, PGI2) and subtypes of thereof, and, LTB4.

Biomarkers and LD

The immune system produces biomarkers that can increase or decrease in response to an infection, for example, LD. For example, excess interferon gamma (INF-γ) has been found in early Lyme disease patients with an erythema migrans (EM) rash. However, other cytokines, e.g., interleukin-1 beta (IL-1β) and tumor necrosis factor-alpha (TNF-α) were found to be more prevalent in later, chronic LD infection. Although this distinguishes groups on a statistical basis, it is not sensitive or specific enough to diagnose or specify treatment of subjects. It has now been found that the identification of the presence of multiple biomarkers expressed in specific combination—a biomarker signature—may be utilized to diagnose and treat early LD. Further, biomarker signatures may define whether an infected subject, human or other species, has LD and requires treatment. The terms "subject" as used herein refers to a mammal including a non-primate (e.g., cow, pig, horse, dog, cat, rat, deer, and mouse) and a primate (e.g., monkey and human). Single host response markers are rarely sufficient for accurate diagnosis; rather, as disclosed herein, it is the mathematically defined relationship among them described by logic formula equation that is derived from logistic regression among the combination of two or more, preferably at least four, and more preferably 10-12 of these markers that reveals the underlying network of LD host response that is critical for diagnosis and treatment. The following biomarkers are examples of analytes that provide information about the immune network response: CTACK, GROa, IL.2Ra, IL.16, IL.18, M.CSF, MIF, MIG, b.NGF, SCF, SCGF.b, SDF.1a, TNF.b, TRAIL, HGF, IFN.a2, IL.1B, IL.4, IL.6, IL.10, IL.17A, IL.31, IL.33, IFN.g, sCD40L, TNF.a, PDGF.bb, IL.1ra, IL.2, IL.5, IL.7, IL.8,IL.9, IL.12.p70, IL.13, Eotaxin, FGF.basic, G.CSF, GM.CSF, IP.10, MCP.1.MCAF, MIP.1a, MIP.1b, RANTES, VEGF, a.2. macro, globulin, CRP, Ferritin, Fibrinogen, Procalcitonin, Serum, Amyloid.A, Tissue, Plasminogen, Activator, CCL17.TARC, cd4, cd8, and cd4cd8 ratio, This invention may include other markers that similarly provide information about the underlying immune network and is not restricted to the specific biomarker examples provided herein. The utility of the invention is founded in the biomarker signature comprising. The methodology and assay resulting from the discovery of biomarker signatures may be used as the sole evaluation for a subject, or alternatively, may be used in combination with other diagnostics and treatment methodologies.

Biomarker Assessment and Evaluation

For purposes of assessment and evaluation, choice of biomarkers was based evidence of ability to separate LD subjects from controls in a 1) t-test or 2) ROC curve or 3) known to be produced or related to early immune responses. The receiver operating characteristic (ROC) curve or table is a statistical tool commonly used to evaluate the utility in clinical diagnosis of a proposed assay. The ROC addresses the sensitivity and the specificity of an assay. Therefore, sensitivity and specificity values for a given combination of biomarkers are an indication of the accuracy of the assay. The ROC curve is the most popular graphical tool for evaluating the diagnostic power of a clinical test. A number representing the fraction of the total graphical area under the curve (AUC) can be derived, is a widely used method of evaluating a potential diagnostic tool. Sometimes the AUC of a subset of the space is used. This type of evaluation looks at the sensitivity at each specificity of the test. Sensitivity relates to the ability of a test to correctly identify a condition, while specificity relates to the ability of a test to correctly exclude a condition. The present invention has employed this type of analysis to evaluate a unique biomarker signature from which a combination of two or more biomarkers is chosen, that may be effectively used in the diagnosis of early LD.

In use, the present invention creates a new derived number, output value, or score that can be treated as a single "test" for ROC curve and AUC analysis. This approach allows use of these methods and comparison with other clinical assays that typically are the results of single analytes. The results from the statistical analysis performed provide an output value or score that can be directly translated into the probability that a sample comes from a subject with LD. A score above a certain cutoff threshold, for example 50% is indicative of the presence of LD and a score below the cutoff threshold is indicative of the absence of LD. However, depending on the clinical situation physicians and/or subjects can choose to favor sensitivity, for example by using a threshold of 40% probability of having LD or specificity, for example by using a threshold of 60% probability of having LD. Higher sensitivity might be chosen, for example, in a highly endemic area when a diagnosis of an illness is sought, while higher specificity might be chosen, for example, in a screening situation or other situation of lower incidence, or epidemiologic work. Nonetheless, the AUC can still serve as a general measure of the accuracy of the derived score or derived probability. These numbers derived, via the methods in the examples, provide excellent AUCs, while single biomarkers do not. Thus, scores indicative of presence or absence of the LD are provided as is a method of diagnosis and that indicates appropriate treatment.

Unique biomarker signatures have been discovered in LD providing a means of early screening, diagnosis, and treatment. Early diagnosis is important because early treatment has the greatest chance of a cure; delayed treatment is associated with the severe chronic form of the disease. LymeDisease.org published a Health Policy paper based on a survey of Lyme patients, many of whom might not have had such severe symptoms had they been diagnosed and treated promptly, which reported that in this group: 84% not diagnosed within 4 months of onset; 25% had been on disability; 50% see more than 7 physicians before diagnosis; 95% had LD for more than 2 years; 65% cut back on school or work; and, 25% were children.

Disclosed herein are particular biomarkers found to be associated with LD and which can be used in combination as a biomarker signature for diagnosis and treatment of LD. More specifically, disclosed herein are equations based on specific quantitative biomarker values found to be associated with LD immune phenotype, and thus LD.

Such biomarker signatures may be useful for predictive purposes, diagnostic purposes, treatment purposes, for methods for predicting treatment response, methods for monitoring disease progression, and methods for monitoring treatment progress, as described in further detail herein. Further applications of the LD biomarker signature include assays as well as kits for use with the methods described herein.

As used herein, the verb "comprise" as is used in this description and in the claims and its conjugations are used in its non-limiting sense to mean that items following the word are included, but items not specifically mentioned are not excluded. In addition, reference to an element by the indefinite article "a" or "an" does not exclude the possibility that more than one of the elements are present, unless the context clearly requires that there is one and only one of the elements. The indefinite article "a" or "an" thus usually means "at least one".

As used herein, a "sample," such as a biological sample, is a sample obtained from a subject. As used herein, biological samples include all clinical samples including, but not limited to, cells, tissues, and bodily fluids, such as: saliva, tears, breath, blood; derivatives and fractions of blood, such as filtrates, dried blood spots, serum, and plasma; extracted galls; biopsied or surgically removed tissue, including tissues that are, for example, unfixed, frozen, fixed in formalin and/or embedded in paraffin; tears; milk; skin scrapes; nails, skin, hair; surface washings; urine; sputum; bile; bronchoalveolar fluid; pleural fluid, peritoneal fluid; cerebrospinal fluid; prostate fluid; pus; or bone marrow. In a particular example, a sample includes blood obtained from a subject, such as whole blood or serum. In another example, a sample includes cells collected using an oral rinse.

Methods for diagnosing, predicting, assessing, and treating early LD in a subject include detecting the presence or absence of one or more biomarker signatures described herein, in a subject's sample. The biomarker(s) may be isolated or, more typically quantified without isolation, from a biological sample using standard techniques. The sample may be isolated from the subject and then directly utilized in a method for determining the level of the biomarkers, or alternatively, the sample may be isolated and then stored (e.g., frozen) for a period of time before being subjected to analysis.

In some embodiments, the present invention is directed to a method of diagnosing and treating LD in a subject comprising the steps of:
obtaining a sample from the subject;
detecting in the sample the presence of a biomarker signature; and
administering a therapeutic treatment to the subject based on the biomarker signature detection results.

In some embodiments, predicting an increased likelihood of the subject having LD based on the presence or absence of a biomarker signature is further included.

In some embodiments, combinations of two, three, four, five, six, seven, eight, nine, ten, eleven, twelve, or more biomarkers may be detected in the sample from the subject.

In some embodiments, a method of diagnosing and treating LD in a subject comprising the steps of:
obtaining a sample from the subject;
detecting in the sample the expression levels of a combination of two or more analytes selected from the group consisting of IL.1B, IL.2, IL.4, IL.6, IL.8, IL.10, IFN.g, MCP.1, TNF.a, VEGF, CRP, IL.5, GM.CSF, MIP.1a, MIG, b.NGF, IP.10, MIP.1b, Ferritin, Fibrinogen, SAA, CCL19, PDGF.bb, Procalcitonin, and CTACK, wherein the detection of the presence or absence of the combination of biomarkers is indicative of LD infection; and
administering a therapeutic treatment to the subject.

Another embodiment of the invention includes an assay and/or kit for diagnosing an early LD infection comprising reagents, probes, buffers; antibodies, or other agents that bind to biomarkers; signal generating reagents, including but not limited fluorescent, enzymatic, electrochemical; or separation enhancing methods, including but not limited to beads, electromagnetic particles, nanoparticles, binding reagents, for the detection of a combination of two or more biomarkers indicative thereof. In some embodiments, the probe and the signal generating reagent may be one in the same. The agents that bind to biomarkers provided as part of an assay or kit further comprise agents that correlate directly to said biomarkers, Techniques of use in all of these methods are discussed below. Numerous researchers have looked at biomarkers in a wide variety of disease, and specifically in LD. See, for example, Soloski et al. ((2014) PLoS ONE 9(4):e93243), hereby incorporated by reference in its entirety, including supplemental materials and deposited materials, as an example study of 65 cytokines. Soloski teaches that nearly half of the LD patients studied have patterns of cytokines that they call "low responders" that are similar to controls without disease. Despite sophisticated analysis using statistical methods and elegant "heat maps," the Soloski team found no biomarker patterns diagnostic of LD. In contrast, the instant invention applies alternative mathematical and statistical approaches on carefully selected subsets and discloses the unexpected results of exhibited biomarker patterns that reveal underlying immune networks and provide equations that allow accurate classification of subjects indicative of the likelihood of disease.

Identification of Biomarker Signature(s):

The statistical methodology for biomarker signature determination included the analysis of data from 65 analytes, or biomarkers, from the blood of 44 subjects identified as having Lyme disease and 23 control subjects. Sixteen of the analytes were dropped from the analysis process due to an excessive number of missing values or an excessive number of values below the level of detection (LOD).

Logistic Regression

The first approach was to perform logistic regression (LR) of Lyme disease status (Lyme or Control) on selected sets ("models") of biomarkers (also referred to as independent variables, or IVs) to determine if the IVs adequately separated LD from controls. Logistic regression can be performed either using the original measured values of IVs, or each IV can be scaled (by subtracting its mean and then dividing by its standard deviation) prior to performing the regression. In either case, the result of LR is a linear function of the IVs, whose coefficients depend on Lyme disease status and the values of the IVs for each subject. This linear function predicts the (log) odds that a subject has Lyme disease. The predictive results are identical whether raw or scaled values are used, but the specific equations that result from the two approaches can be different. Logistic regression may optionally include additional variables, e.g., subject age, gender, BMI, genotype, and/or geographical region.

Each model results in a different equation for predicting Lyme disease status following the logistic regression process. Thus, multiple IVs are used in a model that has predictive value far in excess of individual analytes. It is only through the IV's, or biomarker's, inclusion in the equation that the role of that analyte to predicting Lyme disease is useful.

Once LR has been performed, the results can be handled in several ways. To make actual predictions of Lyme disease status, a specific (log) odds threshold is chosen, and those subjects whose odds are higher than the threshold are declared to have Lyme disease and the remainder declared not to have Lyme disease. Typically the probability threshold is between 40-60%. While most typically it is 50%, an embodiment may include choosing a low threshold to increase the sensitivity even at the expense of specificity.

One unique aspect and institution of personalized medicine is to allow the physician of subject to choose the sensitivity and specificity appropriate for each subject and/or clinical condition. By way of example, a threshold may be based on the comparative cost of false positive versus false negative predictions. If the costs of both types of misdiagnosis are roughly equal, a log odds threshold of 0 (corresponding to a 0.50 LD probability) may be used. If high sensitivity (low false negative rate) is chosen as more desirable, a positive log odds threshold may be chosen. More specifically, the desire to miss no more than 5% of LD cases would require a log odds threshold of 2.94.

In order to evaluate the accuracy of the test, compared were the known condition of each subject with the predicted condition obtained, and the sensitivity and specificity of the LR a chosen threshold. A second process is to plot sensitivity versus specificity for every potential threshold value or selected values such as every 5%. The resulting plot, referred to as a receiver operating characteristic (ROC) curve, provides a synoptic view of the effectiveness of the particular combination of IVs. One convenient way of summarizing the entire ROC curve is by taking the area under it (AUC). Another is to examine the area under the critical region reflecting the specificities above 80% (HS ROC).

Several candidate models (sets of IVs) were selected based on different criteria, such as having t-test scores with p values below certain levels, and/or being involved in the early stages of immune response, and/or being easily measured clinically. For each such model LR was performed and plotted the resulting ROC curve, ROC table, AUC and HS-AUC were evaluated thereby providing a visual and or numerical means of comparing the benefits and/or accuracy of the different IV candidate sets.

Based on the size of the data set used in the analysis, the number of IVs in any candidate set was limited to approximately 12, in order to avoid overfitting of the LR results. To check for overfitting, several cross validation tools were applied to each LR model. As another means of reducing overfitting several standard procedures for reducing the dimensionality of the LR model were examined.

Stepwise (logistic) regression reduces dimensionality by eliminating an IV from the model if its presence does not significantly improve the performance of the model. Principal components and partial least squares (logistic) regression, reduce dimensionality by means of procedures that take into account the manner in which the IVs correlate with one another (and with the response variable, in the case of partial least squares). Partial least squares was chosen as the most preferred means of LR in the instant case.

Assays, Kits, and Apparatuses:

An assay for analysis of subject samples for diagnosing, staging, and/or treating LD is provided. An assay may be provided individually or as part of a kit. Typically, an assay comprises at least one protein probe (detection agent) for a protein such as an antibody, aptamer or other protein binding compound or at least one pair of reagents, said probe or reagents including antibodies, aptamers, or other biomarker binding materials; and a substrate or homogenous reaction for the detection of an analyte. An assay for a biomarker signature may contain multiple probes corresponding to multiple analytes. The substrate may comprise, for example, beads, plates, glass slides, protein spots in microtiter wells, or other wells, or a microarray. The assay and/or kit may further comprise agents that generate detectable signals, where the agent may include, for example, light, enzyme reactions, electrochemical changes, fluorescent materials, plasmon resonance, magnetic signals, light, interference with light, or other signals known in the art. The probes may be bound to a substrate so that a change is immediately detectable by mass cantilevers, optical changes such as reflectance or interference, or other changes when the analyte is bound to the probe on the substrate. In some methods of quantifying analytes a competitive assay. Assays and/or kits optionally include buffers, vials, microtiter plates or other solid substrates, and instructions for use. In some examples known in the art, assays and/or kits are intended to perform homogeneous assays, and thus, do not contain reagents or methods to physically separate the bound and unbound materials. Such assays and/or kits may use fluorescent energy transfer or micro environment transfer of substrates.

In the assay and/or kit aspect of the invention, provided is a substrate comprising detection agents specific for at least two biomarkers selected from IL.1B, IL.2, IL.4, IL.6, IL.8, IL.10, IFN.g, MCP.1, TNF.a, VEGF, CRP, IL.5, GM.CSF, MIP.1a, MIG, b.NGF, IP.10, MIP.1b, Ferritin, Fibrinogen, SAA, CCL19, PDGF.bb, Procalcitonin, and CTACK for use in a method for diagnosing LD in a subject according to the present invention. Preferably, the substrate has at least two probes immobilized thereon, more preferably three, four, or more probes, wherein each probe is specific to an individual biomarker comprising the biomarker signature. As used herein, the term "specific" means that the probe binds only to one of the biomarkers of the invention with relatively little other binding. In some embodiments, higher specificity of the probe reactions is obtained by using probe pairs and only recording a positive signal only if both bind, this is typically a "sandwich assay." Kits of the present invention may further comprise additional reagents, substrate/reaction surfaces, and/or instructions for use.

Preparation of Sample(s) for Analysis:

Samples may be prepared for analysis using any technique known to those skilled in the art for determining the presence of biomarkers While cell extracts can be prepared using standard techniques in the art, the methods generally use serum, blood filtrates, blood spots, plasma, saliva, tears, or urine prepared with simple methods such as centrifugation and filtration. The use of specialized blood collection tubes such as rapid serum tubes containing a clotting enhancer to speed the collection of serum and agents to prevent alteration of the biomarkers is one preferred method of preparation. Another preferred method utilizes tubes containing factors to limit platelet activation, one such tube contains citrate as the anticoagulant and a mixture of theophylline, adenosine, and dipyrimadole.

The preferred methodology is based on the overall concept of immune-detection. Such detection may be performed in a laboratory, point of care, clinical, or other setting, and may be incorporated into transportable or hand-held devices. A quantitative immunoassay, e.g., ELISA or its equivalent, may be used to detect the amount of protein. A multi-analyte method of analysis enabling several proteins to be detected and quantified simultaneously may be used.

Biomarker Detection

Methods for detecting biomarkers, e.g., cytokines, chemokines and prostaglandins in samples are well known in the art. In one example, detection includes detecting expression of a biomarker signature, wherein said signature is comprised of a combination of at least two or more biomarkers. Detection can include classic sandwich or competitive immunoassays, these may be done in ELISA format or any of numerous commercial and available research methods known in the art, such as, Randox, Luminex, Quanterix, Cyplex, MagArray, plasmon resonance methods, and any method that detects the presence of a biomarker by the binding of a antibody, aptamer, or other binding molecule.

Analysis

For use of the two or more biomarkers in the diagnostic method of the present invention a suitable mathematical method, e.g., such as logistic regression is used. Logistic regression is run on the chosen biomarker values on the LD subjects and control subjects. An ROC curve may be used to assess the relationship between sensitivity and specificity.

Other embodiments in accordance with the principles of the present invention include, for example, a system for determining whether a subject possesses a biomarker signature and/or score indicative of initial diagnosis of acute or chronic disease, continuing presence of disease and/or response to treatment. For example, the system may include an on-site storage device or central server configured to store data produced from the sample suspected of LD infection, as well as evaluation algorithms for determination of score and subsequent treatment. Such systems may not include the algorithm, but may further include a processor that communicates with the storage device or server, wherein the processor and/or server executes software to obtain and/or scale data produced from the sample, process the data, and determine a score indicative of LD status. In some embodiments, both systems containing computation ability and communication ability with a server in real or delay time may occur.

The present invention is further illustrated by the following examples that should not be construed as limiting. The contents of all references, patents, and published patent applications cited throughout this application, as well as any FIGURES, are incorporated herein by reference in their entirety for all purposes.

Provided is a method for diagnosing and treating a subject suspected of having LD, comprising determining the expression of at least two biomarkers in a sample, and mathematically establishing the significance of the concentration of the biomarkers, wherein the at least two biomarkers are selected from IL.1B, IL.2, IL.4, IL.6, IL.8, IL.10, IFN.g, MCP.1, TNF.a, VEGF, CRP, IL.5, GM.CSF, MIP.1a, MIG, b.NGF, IP.10, MIP.1b, Ferritin, Fibrinogen, SAA, CCL19, PDGF.bb, Procalcitonin, and CTACK.

In a preferred embodiment, the at least two biomarkers are selected from the group consisting of CRP, IL.5, GM.CSF, MIP.1a, CTACK, and Procalcitonin. In another preferred embodiment, the at least two biomarkers are selected from the group consisting of CRP, IL.5, GM.CSF, and MIP.1a. More preferably, the at least two biomarkers are selected from the group consisting of MIG, b.NGF, IL.1B, IL.6, IL19, MIP.1b, CRP, Ferritin, Fibrinogen, SAA, and CCL19.MIP3B. Even more preferably, the at least two biomarkers are selected from the group consisting of CRP, IL.1B, IL.2, IL.4, IFN.g, and VEGF. Most preferably, the at least two biomarkers are selected form the group consisting of CRP, IL.1B, IL.2, IL.4, IL.6, IL.8, IL.10, IFN.g, MCP.1.MCAF, TNF.a and VEGF. Combinations of three or more biomarkers may also be preferred as they evidence some of the highest sensitivity and specificity. Said preferred biomarker combinations are listed in Table 2, corresponding to examples 2-6, wherein sensitivity, specificity, and AUC data for such combinations are listed.

TABLE 2

AUC, Cross Validation and Receiver Operator Characteristics

| Example | AUC | Xval LOO | Xval 10x | Sensitivity at Specificity (ROC) | | | | |
|---|---|---|---|---|---|---|---|---|
| | | | | 1 | 0.95 | 0.9 | 0.85 | 0.8 |
| 2 | 0.992 | 0.83 | 0.8 | 0.95 | 0.98 | 0.98 | 0.98 | 0.98 |
| 3 | 0.985 | 0.83 | 0.77 | 0.88 | 0.9 | 0.93 | 0.95 | 1 |
| 4 | 0.971 | 0.79 | 0.79 | 0.73 | 0.8 | 0.9 | 0.95 | 0.95 |
| 5 | 0.958 | 0.83 | 0.84 | 0.78 | 0.85 | 0.88 | 0.9 | 0.93 |
| 6 | 0.98 | 0.84 | 0.81 | 0.88 | 0.9 | 0.95 | 0.95 | 0.95 |

Biomarker concentrations can be determined by contacting the sample with a substrate having probes specific for each of the biomarkers includes in the biomarker signature. Biomarker and respective probe interactions may be monitored and quantified using various techniques that are well-known in the art. For biomarker signature quantification, a solid substrate device is preferred, many of which are known in the art.

Data corresponding to a specific set of biomarkers, the model, was analyzed with mathematical models and algorithms disclosed herein, thereby generating a sensitive and specific assay for Lyme disease. All of the data were analyzed by using logistical regression, and/or Support Vector Machines (SVM). ROC analysis was used to estimate the sensitivity/specificity relationship for each analysis performed, the results of which are summarized herein and set forth in detail in Table 2. In order to evaluate the robustness of the methods, the available data sets were randomly divided into training and validation sets 1000 times. The AUCs for each using various methods is presented. Thus, although SVM produced the highest AUC on training data, regression methods were the most robust in use, proving the equations, especially the one generated by logistic regression, are not simply a fit for the training data but a useful method to parse the validation/testing set, and thus, validated as clinically relevant.

Additional methods of statistical analysis known in the art, including Principal components analysis (PCA), principal coordinates analysis, principal coordinates regression, partial least squares, independent coordinates analysis, forward stepwise regression, random forest analysis, and/or cluster analysis may also be used to analyze data, either alone or in combination, and are included in this invention.

The performance of each non-obvious equation in the examples below was evaluated by area under the receiver operating characteristic curves (AUC) which ranged from a random 0.5 to 0.99. Some biomarkers negatively correlated with LD. Examples of biomarker signatures evaluated as described herein are set forth in Examples 2-5 and have an AUC≥0.95 for the logistic regression model.

Example 1 Stepwise Regression

In this example, analytes were restricted to those listed in Table 1. Stepwise regression models were considered as well as "all variables" models. Stepwise regression is a method for including only those variables in the model that significantly improve the results over the situation in which the variable is left out. This method reduces dimensionality with little impact on the effectiveness of the analysis.

Table 1 shows the AUCs of full and stepwise regression for analyte combinations shown.

TABLE 1

AUCs Full and Stepwise Regression

| | All Variables | Stepwise |
|---|---|---|
| IL.1B, IL.2, IL.4, IL.6, IL.8, IL.10, IFN.g, MCP.1, TNF.a, and VEGF | .9523 | .9438 |
| CRP, IL.1B, IL.2, IL.4, IL.6, IL.8, IL.10, IFN.g, MCP.1, TNF.a, and VEGF | .9915 | .9852 |

By way of example, a panel consisting of CRP, IL.1B, IL.2, IL.4, IL.6, IL.8, IL.10, IFN.g, MCP.1, TNF.a, and VEGF resulted in an AUC of 0.992. Further limiting the panel to CRP, IL1.B, IL.2, IL.4, IFN.g, and VEGF resulted in an AUC of 0.985. The novel methodology of analysis is, therefore, robust. It is not unduly sensitive to any one variable, leaving out any of the variables in this example resulted in a decrease of only 0.04 in the respective AUCs. These are non-limiting examples of panels that measure the biomarker signature(s) in LD versus controls, and thus, effectively determine the presence of organisms, such as spirochetes.

These results identify an immune network and anomalies unique to Lyme disease several illustrations of models (sets of biomarkers) detecting the anomaly in the network are provided hereinbelow. Several biomarker signatures, each identifying the immune network associated with the diagnosis of LD can be used to identify those with acute infection.

Example 2 Model Comprising 11 Biomarker Analytes

Biomarkers were chosen based on their known immunologic properties. The following equation includes the specific biomarkers and the coefficients derived by logistic regression. By way of example, a logistic regression equation applicable to the present invention for the biomarker combination of CRP, IL.1B, IL.2, IL.4, IL.6, IL.8, IL.10, IFN.g, MCP.1.MCAF, TNF.a and VEGF for indication of LD in a subject where Logit=sum of coefficients derived from logistic regression multiplied by [analyte concentrations] is calculated as follows:

$$\text{Logit}=\log(\text{Probablility}/(1-\text{Probablility}))=-5.90+\\0.00098*\text{CRP}+60.3*\text{IL.1B}+0.125*\text{IL.2}-\\0.736*\text{IL.4}+0.525*\text{IL.6}-0.294*\text{IL.8}+\\0.563*\text{IL.10}-7.21*\text{IFN.g}+0.234*\text{MCP.1.MCAF}+\\0.639*\text{TNF.a}-0.0921*\text{VEGF}$$

The AUC of this equation was 0.992 and LOO and 10× cross validation showed values above 0.8 indicating robustness. Based on an outcome of carrying out the method of the invention wherein the score is indicative of LD, then the subject may be treated accordingly.

Table 2 details the sensitivity at various clinically important, specificities, and AUC of the exemplary combinations of biomarkers for LD diagnosis in the preferred models of biomarkers illustrated in Examples 2-5. By combining 11 biomarkers selected from the group consisting of IL.1B, IL.2, IL.4, IL.6, IL.8, IL.10, IFN.g, MCP.1, TNF.a, VEGF, CRP, IL.5, GM.CSF, MIP.1a, MIG, b.NGF, IP.10, MIP.1b, Ferritin, Fibrinogen, SAA, CCL19, PDGF.bb, Procalcitonin, and CTACK, a test with high diagnostic performance is achieved. Key to the present invention is the power of biomarker signatures to diagnose early LD through high specificity and sensitivity. This aspect of the invention facilitates clinical diagnosis and informs subsequent treatment decisions.

Example 3 Model Comprising 12 Biomarker Analytes

Using statistical methods, the top 12 analytes were chosen as a model. A logistic regression equation applicable to the present invention at for the biomarker combination of MIG, b.NGF, IL.1B, IL.6, IL19, MIP.1b, CRP, Ferritin, Fibrinogen, SAA, and CCL19.MIP3B for indication of LD in a subject is calculated as follows:

$$\text{Logit} = \log(\text{Probablility}/(1-\text{Probablility})) = -6.24 - 0.00447*\text{MIG} + 0.336*b.\text{NGF} + 0.215*\text{IL.1B} + 0.330*\text{IL.6} + 0.00451*\text{IP.10} - 0.00843*\text{MIP.1b} + 0.0008769*\text{CRP} + 0.0000215*\text{Ferritin} + 0.0000896*\text{Fibrinogen} - 0.000951*\text{Serum.Ameyloid.A} + 0.0124*\text{CCL19.MIP3B}$$

The AUC of this equation was 0.971 and cross validation showed accuracy of 0.79. Based on an outcome of carrying out the method of the invention wherein the score is indicative of LD, then the subject may be treated accordingly. By combining 12 biomarkers selected from the group consisting of IL.1B, IL.2, IL.4, IL.6, IL.8, IL.10, IFN.g, MCP.1, TNF.a, VEGF, CRP, IL.5, GM.CSF, MIP.1a, MIG, b.NGF, IP.10, MIP.1b, Ferritin, Fibrinogen, SAA, CCL19, PDGF.bb, Procalcitonin, and CTACK, a test with high diagnostic performance is achieved.

Example 4 Model Comprising 6 Biomarker Analytes

Examination of a smaller set of analytes, six, provided slightly reduced accuracy. A logistic regression equation applicable to the present invention for the biomarker combination of CRP, IL.1B, IL.2, IL.4, IFN.g, and VEGF for indication of LD in a subject is calculated as follows:

$$\text{Logit} = \log(\text{Probablility}/(1-\text{Probablility})) = -4.10 + 0.00085*\text{CRP} + 40.47*\text{IL.1B} + 0.311*\text{IL.2} - 0.525*\text{IL.4} - 5.58*\text{IFN.g} - 0.0923*\text{VEGF}$$

The AUC of this equation=0.9852 and cross validation showed values averaging about 0.8, indicating robustness. Based on an outcome of carrying out the method of the invention wherein the score is indicative of LD, then the subject may be treated accordingly. By combining 6 biomarkers selected from the group consisting of IL.1B, IL.2, IL.4, IL.6, IL.8, IL.10, IFN.g, MCP.1, TNF.a, VEGF, CRP, IL.5, GM.CSF, MIP.1a, MIG, b.NGF, IP.10, MIP.1b, Ferritin, Fibrinogen, SAA, CCL19, PDGF.bb, Procalcitonin, and CTACK. a test with high diagnostic performance is achieved.

Example 5 Model Comprising 4 Biomarker Analytes

A set of markers known in the art to reflect the immune system initial response was examined. A logistic regression equation applicable to the present invention for the biomarker combination of CRP, IL.5, GM.CSF, and MIP.1a for indication of LD in a subject is calculated as follows:

$$\text{Logit} = \log(\text{Probablility}/(1-\text{Probablility})) = -3.59 + 0.000543*\text{CRP} + 0.344*\text{IL.5} - 1.03*\text{GM.CSF} + 0506*\text{MIP.1a}$$

The AUC of this equation=0.958 with a cross validation of 0.83-0.84. Based on an outcome of carrying out the method of the invention wherein the score is indicative of LD, then the subject may be treated accordingly. By combining 4 biomarkers selected from the group consisting of IL.1B, IL.2, IL.4, IL.6, IL.8, IL.10, IFN.g, MCP.1, TNF.a, VEGF, CRP, IL.5, GM.CSF, MIP.1a, MIG, b.NGF, IP.10, MIP.1b, Ferritin, Fibrinogen, SAA, CCL19, PDGF.bb, Procalcitonin, and CTACK, a test with high diagnostic performance is achieved.

Example 6 Model Comprising 6 Biomarker Analytes

A set of markers known in the art to reflect the immune system initial response was examined. A logistic regression equation applicable to the present invention for the biomarker combination of CRP, IL.5, GM.CSF, MIP.1a, CTACK, and Procalcitonin for indication of LD in a subject is calculated as follows:

$$\text{Logit} = \log(\text{Probability}/(1-\text{Probability})) = 6.58 + 0.000665*\text{CRP} - 0.0872*\text{IL.5} - 1.03*\text{GM.CSF} + 0.722*\text{MIP.1a} - 0.0513*\text{CTACK} - 0.000919*\text{Procalcitonin}$$

The AUC of this equation=0.98 with a cross validation of 0.81-0.84. Based on an outcome of carrying out the method of the invention wherein the score is indicative of LD, then the subject may be treated accordingly. By combining 5 biomarkers selected from the group consisting of IL.1B, IL.2, IL.4, IL.6, IL.8, IL.10, IFN.g, MCP.1, TNF.a, VEGF, CRP, IL.5, GM.CSF, MIP.1a, MIG, b.NGF, IP.10, MIP.1b, Ferritin, Fibrinogen, SAA, CCL19, PDGF.bb, Procalcitonin, and CTACK, a test with high diagnostic performance is achieved.

Although the examples of the principles of the present invention have been described with respect to LD and treatment known to be effective therefor, now or in the future, it should be understood that the principles may be applied to other disease and/or infections exhibiting similar symptoms and/or signatures for diagnosis, differential diagnosis, and/or treatment.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entirety for all purposes.

The publications discussed herein are provided solely for their disclosure prior to the filing date of the present application. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features set forth herein.

Abbreviations

IL.1B—interleukin-1B
IL.2—interleukin-2
IL.4—interleukin-4
IL.6—interleukin-6

IL.8—interleukin-8
IL.10—interleukin-10
IFN.g—interferon gamma
MCP.1—monocyte chemoattractant protein 1
TNF.a—tumor necrosis factor alpha
VEGF—vascular endothelial growth factor
CRP—c-reactive protein
IL.5—interleukin-5
GM.CSF—granulocyte macrophage colony stimulating factor
MIP.1a—macrophage inflammatory protein-1 alpha
MIG—monokine induced by gamma-interferon
b.NGF—beta-nerve growth factor
IP.10—interferon inducible protein 10
MIP.1b—macrophage inflammatory protein-1 beta
SAA—serum amyloid A
CCL19—chemokine (c-c motif) ligand 19
PDGF.bb—platelet-derived growth factor bb
CTACK.—cutaneous T-cell attracting chemokine

What is claimed is:

1. A method of analyzing a sample, comprising: a) obtaining a sample from a subject suspected of having Lyme disease; and b) detecting in the sample the presence of a biomarker signature comprising a combination of four to twenty-five analytes including Interleukin 6 (IL.6), Cutaneous T cell-attracting chemokine (CTACK), Fibrinogen, and Nerve growth factor beta (b.NGF).

2. The method of claim 1, wherein detecting the presence of the biomarker signature comprises generating a complex between at least one detection agent and said four to twenty-five analytes.

3. The method of claim 1, wherein said biomarker signature further comprises one or more additional analytes selected from the group consisting of Interleukin 1 beta (IL.1B), Interleukin 2 (IL.2), Interleukin 4 (IL.4), Interleukin 8 (IL.8), Interleukin 10 (IL.10), Interferon gamma (IFN.g), Monocyte chemoattractant protein-1 (MCP.1), Tumor necrosis factor alpha (TNF.a), Vascular endothelial growth factor (VEGF), C-reactive protein (CRP), Interleukin 5 (IL.5), Granulocyte-macrophage colony-stimulating factor (GM.CSF), Macrophage inflammatory protein 1alpha (MIP.1a), Monokine induced by gamma (MIG), Interferon gamma-induced protein 10 (IP.10), Macrophage inflammatory protein 1beta (MIP.1b), Ferritin, Serum amyloid A1 (SAA), Chemokin (C-C motif) ligand 19 (CCL19), Platelet-derived growth factor-BB (PDGF.bb), and Procalcitonin.

4. The method of claim 3, wherein the four to twenty-five analytes comprise CRP, IL.5, GM.CSF, and MIP.1a.

5. The method of claim 3, wherein the four to twenty-five analytes comprise IL.1B, IL.2, IL.4, IFN.g, VEGF, and CRP.

6. The method of claim 3, wherein the four to twenty-five analytes comprise IL.1B, IL.6, CRP, MIG, b.NGF, IP.10, MIP.1b, Ferritin, Fibrinogen, SAA, and CCL19.

7. The method of claim 3, wherein the four to twenty-five analytes comprise IL.1B, IL.2, IL.4, IL.6, IL.8, IL.10, IFN.g, MCP.1, TNF.a, VEGF, and CRP.

8. The method of claim 3, wherein the four to twenty-five analytes comprise CRP, IL.5, GM.CSF, MIP.1a, CTACK, and Procalcitonin.

* * * * *